(12) United States Patent
Huang (10) Patent No.: US 10,792,240 B2
(45) Date of Patent: Oct. 6, 2020

(54) SKINCARE PRODUCT AND METHOD OF PREPARATION THEREOF

(71) Applicant: Xi Huang, Montvale, NJ (US)

(72) Inventor: Xi Huang, Montvale, NJ (US)

(73) Assignee: Fe:I Beauty Tech, Inc., Wilmington, DE (US)

(*) Notice: Subject to any disclaimer, the term of this patent is extended or adjusted under 35 U.S.C. 154(b) by 67 days.

(21) Appl. No.: 14/380,679

(22) PCT Filed: Feb. 22, 2013

(86) PCT No.: PCT/IB2013/051438
§ 371 (c)(1),
(2) Date: Aug. 22, 2014

(87) PCT Pub. No.: WO2013/124821
PCT Pub. Date: Aug. 29, 2013

(65) Prior Publication Data
US 2015/0024016 A1    Jan. 22, 2015

(30) Foreign Application Priority Data
Feb. 23, 2012 (CN) .......................... 2012 1 0041549

(51) Int. Cl.
*A61K 8/67* (2006.01)
*A61Q 19/08* (2006.01)
(Continued)

(52) U.S. Cl.
CPC ............ *A61K 8/676* (2013.01); *A61K 8/0241* (2013.01); *A61K 8/19* (2013.01); *A61K 8/46* (2013.01);
(Continued)

(58) Field of Classification Search
None
See application file for complete search history.

(56) References Cited

U.S. PATENT DOCUMENTS 3,304,154 A * 2/1967 Kiouzes-Pezas ..... C01F 11/181
264/15
4,251,449 A * 2/1981 Schreur ........................ 549/315
(Continued)

FOREIGN PATENT DOCUMENTS

EP         2264108 A1 * 12/2010 ............. C09C 1/022
WO    WO 9956720 A1 * 11/1999 ............... A61K 8/19
WO      2013/124821 A1    8/2013

OTHER PUBLICATIONS

Andersen "Final report of the safety assessment of L-ascorbic acid, calcium ascorbate, magnesium ascorbate, magnesium ascorbyl phosphate, sodium ascorbate, and sodium ascorbyl phosphate as used in cosmetics," International Journal of Toxicology 24:51-111, 2005.*
(Continued)

*Primary Examiner* — Dominic Lazaro
(74) *Attorney, Agent, or Firm* — Gearhart Law LLC

(57) ABSTRACT

This invention discloses a novel class of skincare products to remove iron in the skin and its preparation method. The core active components, termed as de-ironizing inducers (DII), consist of a reducing agent and a precipitating agent. The reducing agent is selected from vitamin C, vitamin E, glutathione, vitamin A, vitamin D and their derivatives. The precipitating agent is chosen from calcium carbonate, pearl powder, magnesium carbonate, barium carbonate, calcium phosphate, magnesium phosphate, barium phosphate, calcium silicate, magnesium silicate, and barium silicate. Molar ratios of the reducing agent with the precipitating agent range from 1:3-6 and the core components in the skin care product range from 5% to 10% w/w. The PH value of the skincare product is between 6.6 and 7.4. The skin care products can safely and effectively remove iron in the skin, which has been shown to accelerate skin's natural aging and photoaging.

6 Claims, 6 Drawing Sheets

Before use

After use (51) Int. Cl.
A61K 8/19 (2006.01)
A61K 8/46 (2006.01)
A61K 8/02 (2006.01)
(52) U.S. Cl.
CPC ............... *A61K 8/67* (2013.01); *A61K 8/671* (2013.01); *A61K 8/678* (2013.01); *A61Q 19/08* (2013.01); *A61K 2800/412* (2013.01); *A61K 2800/70* (2013.01)

(56) References Cited

U.S. PATENT DOCUMENTS

| | | | | |
|---|---|---|---|---|
| 6,159,504 | A * | 12/2000 | Kumabe | A23D 9/05 424/489 |
| 7,780,977 | B2 | 8/2010 | Inchley | |
| 2005/0084602 | A1 * | 4/2005 | Chen et al. | 426/654 |
| 2009/0041812 | A1 | 2/2009 | Bell | |
| 2010/0086606 | A1 * | 4/2010 | Ogawa | A61K 9/0014 424/489 |
| 2011/0240065 | A1 | 10/2011 | Panandiker et al. | |

OTHER PUBLICATIONS

Kitazawa et al. "Iron chelators may help prevent photoaging," Journal of Cosmetic Dermatology 5(3):210-217, 2006.*
Bissett et al. "Evaluation of a topical iron chelator in animals and in human beings: short-term photoprotection by 2-flurildioxime," Journal of the American Academy of Dermatology 31(4):572-578, 1994.*
Lynch et al. "Interaction of vitamin C and iron," Annals of the New York Academy of Sciences 355:32-44, 1980.*
Gönüllü et al. "Comparing the moisturizing effects of ascorbic acid and calcium ascorbate against tocopherol in emulsions," Journal of Cosmetic Science 57:465-473, 2006.*
Ueno et al. "Drug-incorporating calcium carbonate nanoparticles for a new delivery system," Journal of Controlled Release 103:93-98, 2005.*
Wikipedia, pH, last modified Sep. 15, 2017; https://en.wikipedia.org/wiki/PH.*
Wikipedia "Vitamin C," last updated Sep. 17, 2017; https://en.wikipedia.org/wiki/Vitamin_C.*
Wikipedia "Calcium carbonate," last updated Sep. 9, 2017; https://en.wikipedia.org/wiki/Calcium_carbonate.*
Wikipedia "Retinyl palmitate," last updated Aug. 31, 2017; https://en.wikipedia.org/wiki/Retinyl_palmitate.*
Kumar C, et al., Glutathione revisited: a vital function in iron metabolism and ancillary role in thiol-redox control, The EMBO Journal 2011, 30(10):2044-2056. (Year: 2011).*
Omara FO, Blakley BR: Vitamin E is protective against iron toxicity and iron-induced hepatic vitamin E depletion in mice, The Journal of Nutrition 1993, 123(10):1649-1655. (Year: 1993).*
Chou AC, et al., Abnormalities of iron metabolism and erythropoiesis in vitamin E-deficient rabbits, Blood 1978, 52(1):187-195. (Year: 1978).*
Staab DB, et al., Relationship between vitamin A and iron in the liver, The Journal of nutrition 1984, 114(5):840-844. (Year: 1984).*
Sim JJ, et al., Vitamin D deficiency and anemia: a cross-sectional study, Annals of hematology 2010, 89(5):447-452. (Year: 2010).*
Zimmermann MB, et al., Vitamin A supplementation in children with poor vitamin A and iron status increases erythropoietin and hemoglobin concentrations without changing total body iron, The American journal of clinical nutrition 2006, 84(3):580-586. (Year: 2006).*
Y. Zou, et al., Associations of serum retinal, alpha-tocopherol, and gammatocopherol with biomarkers among healthy Japanese men, Int. J. Environ. Res. Public Health, 11 (2014) 1647-60. (Year: 2014).*

Link, G., et al., Iron loading modifies the fatty acid composition of cultured rat myocardial cells and liposomal vesicles: effect of ascorbate and alpha-tocopherol on myocardial lipid peroxidation, J. Lab. Clin. Med., 114 (1989) pp. 243-249. (Year: 1989).*
M.E. Aliaga, et al., Superoxide-dependent reduction of free Fe(3+) and release of Fe(2+) from ferritin by the physiologically-occurring Cu(I)-glutathione complex, Bioorg. Med. Chem. 19 (2011) pp. 534-541. (Year: 2011).*
M.B. Zimmermann, et al., Vitamin A supplementation in children with poor vitamin A and iron status increases erythropoietin and hemoglobin concentrations without changing total body iron, The Am. J. Clin. Nutr., 84 (2006) pp. 580-586. (Year: 2006).*
L.L. Munasinghe, et al., The Effect of Serum 25-Hydroxyvitamin Don Serum Ferritin Concentrations: A Longitudinal Study of Participants of a Preventive Health Program, Nutrients, 11 (2019). p. 692. (Year: 2019).*
International Search Report dated Jul. 10, 2013, in connection with PCT International Application No. PCT/IB2013/051438, filed Feb. 22, 2013.
Pygmalion, Marie-Jocelyne, et al., "Skin cell protection against UVA by Sideroxyl, a new antioxidant complementary to sunscreens" Free Radical Biology & Medicine 49 (2010) 1629-1637.
J. Jian, E. Pelle, and X. Huang, Iron and menopause: does increased iron affect the health of postmenopausal women? Antioxidants & redox signaling 11 (2009) 2939-43.
E. Pelle, J. Jian, Q. Zhang, N. Muizzuddin, Q. Yang, J. Dai, D. Maes, N. Pernodet, D.B. Yarosh, K. Frenkel, and X. Huang, Menopause increases the iron storage protein ferritin in skin. Journal of cosmetic science 64 (2013) 175-9.
P.M. Harrison, and P. Arosio, The ferritins: molecular properties, iron storage function and cellular regulation. Biochimica et biophysica acta 1275 (1996) 161-203.
N. Abbaspour, R. Hurrell, and R. Kelishadi, Review on iron and its importance for human health. Journal of research in medical sciences : the official journal of Isfahan University of Medical Sciences 19 (2014) 164-74.
A.K. Ziegler, J. Grand, I. Stangerup, H.J. Nielsen, F. Dela, K. Magnussen, and J.W. Helge, Time course for the recovery of physical performance, blood hemoglobin, and ferritin content after blood donation. Transfusion 55 (2015) 898-905.
P. Brissot, A. Pietrangelo, P.C. Adams, B. de Graaff, C.E McLaren, and O. Loreal, Haemochromatosis. Nature reviews. Disease primers 4 (2018) 18016.
M.B. Zimmermann, R. Biebinger, F. Rohner, A. Dib, C. Zeder, R.F. Hurrell, and N. Chaouki, Vitamin A supplementation in children with poor vitamin A and iron status increases erythropoietin and hemoglobin concentrations without changing total body iron. The American journal of clinical nutrition 84 (2006) 580-6.
R. Hurrell, and I. Egli, Iron bioavailability and dietary reference values. The American journal of clinical nutrition 91 (2010) 1461S-1467S.
M.E. Aliaga, C. Carrasco-Pozo, C. Lopez-Alarcon, C. Olea-Azar, and H. Speisky, Superoxide-dependent reduction of free Fe(3+) and release of Fe(2+) from ferritin by the physiologically-occurring Cu(I)-glutathione complex. Bioorganic & medicinal chemistry 19 (2011) 534-41.
L.L. Munasinghe, J.P. Ekwaru, S. Mastroeni, M.F. Mastroeni, and P.J. Veugelers, The Effect of Serum 25-Hydroxyvitamin D on Serum Ferritin Concentrations: A Longitudinal Study of Participants of a Preventive Health Program. Nutrients 11 (2019).
Y. Zou, D.H. Wang, N. Sakano, Y. Sato, S. Iwanaga, K. Taketa, M. Kubo, K. Takemoto, C. Masatomi, K. Inoue, and K. Ogino, Associations of serum retinol, alpha-tocopherol, and gamma-tocopherol with biomarkers among healthy Japanese men. International journal of environmental research and public health 11 (2014) 1647-60.
G. Link, A. Pinson, I. Kahane, and C. Hershko, Iron loading modifies the fatty acid composition of cultured rat myocardial cells and liposomal vesicles: effect of ascorbate and alpha-tocopherol on myocardial lipid peroxidation. The Journal of laboratory and clinical medicine 114 (1989) 243-9.

* cited by examiner

Micron calcium          Submicron calcium

Before use     After use

Fig. 11

SKINCARE PRODUCT AND METHOD OF PREPARATION THEREOF

This application is the § 371 national stage of PCT International Application No. PCT/IB2013/051438, filed Feb. 22, 2013, and designating the United States of America, which claims priority of Chinese Patent Application No. 201210041549.6, filed Feb. 23, 2012, the entire contents of each of which is hereby incorporated by reference in its entirety.

TECHNICAL FIELD

This invention introduces a novel class of skincare products aimed at removing iron in the skin and its preparation method.

TECHNICAL BACKGROUND

Figure 1:
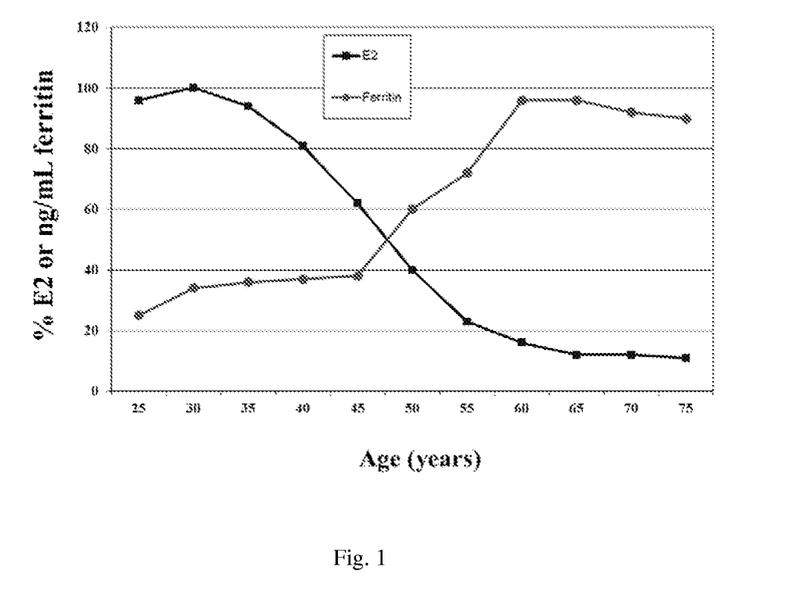
FIG. 1. Concurrent but inverse changes of ferritin versus estrogen during menopausal transition.
Figure 2:
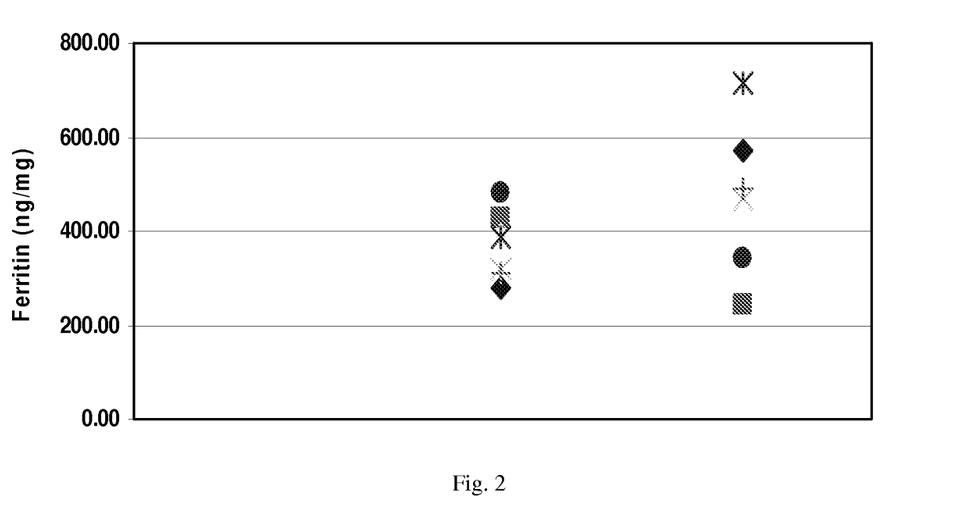
FIG. 2. Differences in levels of ferritin between skin biopsy samples of pre- and post-menopausal women.

Across a woman's lifespan of, menopause has the greatest impact on her health. Due to menopause, the structure and function of the skin is changed more than any other organs'. During menopausal transition and after menopause, the skin becomes thinner, drier, and forms more wrinkles than before menopause. These ailments are mainly due to the decrease in collagen content and its ability to maintain humidity. Therefore, the skin becomes more susceptible to damage caused by environmental factors such as ultraviolet (UV) light and ozone (Miguel, J., Ramirez-Bosca, A., Ramirez-Bosca, J. V., and Alperi, J. D. 2006. *Menopause: a review on the role of oxygen stress and favorable effects of dietary antioxidants. Arch Gerontol Geriatr* 42:289-306). We have found that, after menopause, serum levels of ferritin, an iron storage protein with a capacity of binding up to 4,500 atoms of iron per molecule of ferritin and an indicator of body iron status, were increased 2 to 3-fold (FIG. 1) (Jian, J., Pelle, E., and Huang, X. 2009. *Iron and menopause: does increased iron affect the health of postmenopausal women? Antioxid Redox Signal* 11:2939-2943). Ferritin levels in the skin increase by 40% (FIG. 2). After conversion, we have found that serum ferritin concentration in women is between 0.94-1.3 ng/mg protein. The average concentration of ferritin in postmenopausal skin is about 542 ng/mg protein (FIG. 2). Thus, our study has shown that ferritin concentration in the skin is 400 to 575 times higher than that in serum. Because the human body has no other means to excrete iron, except menstruation and desquamation, skin becomes a very important target for iron in peri- and postmenopausal woman (Andrews, N. C. 1999. *Disorders of iron metabolism. N Engl J Med* 341:1986-1995).

Increased iron can produce large amounts of free radicals in the skin. In addition, we have also found that increased iron sensitizes skin to ultraviolet (UV) light, causing UVA-mediated damage (FIG. 3) (Jian, J., Pelle, E., Yang, Q., Pernodet, N., Maes, D., and Huang, X. 2011. *Iron sensitizes keratinocytes and fibroblasts to UVA-mediated matrix metalloproteinase-1 through TNF-alpha and ERK activation. Exp Dermatol* 20:249-254). For example, after exposure to UVA, matrix metalloproteinase-1 (MMP-1) activity was significantly increased in primary human dermal fibroblast with a high iron concentration when compared to the same fibroblasts containing a normal iron concentration (Jian, J., Pelle, E., Yang, Q., Pernodet, N., Maes, D., and Huang, X. 2011. *Iron sensitizes keratinocytes and fibroblasts to UVA-mediated matrix metalloproteinase-1 through TNF-alpha and ERK activation. Exp Dermatol* 20:249-254). Until now, estrogen deficiency has been considered the main cause of skin aging in middle-aged women (Brincat, M. P., Baron, Y. M., and Galea, R. 2005. *Estrogens and the skin. Climacteric* 8:110-123). However, according to our findings, a decrease in estrogen is not the sole cause of skin thinning, loss of skin elasticity, increase of wrinkle formation, and sensitization of skin to sun exposure in postmenopausal women. Because estrogen replacement therapy increases the risk of cancer (Nelson, H. D., Humphrey, L. L., Nygren, P., Teutsch, S. M., and Allan, J. D. 2002, *Postmenopausal hormone replacement therapy: scientific review. Jama* 288:872-881), it is necessary to develop other alternatives.

Iron is an essential element in the human body. It is an important component of heme, which is responsible for transporting oxygen in red blood cells. Iron is also involved in DNA synthesis and other enzymatic functions. Excess iron is stored in ferritin and excreted through skin desquamation. Ferritin is a major source of iron in the skin and sensitizes skin to sun exposure and oxidative damage. Thus, removal of iron from ferritin can improve skin appearance. At the present, iron chelation is the main therapy to remove iron from human body. However, iron chelators are chemicals, and they have considerable side effects. For example, chelating agents are mainly used for detoxification of metal poisoning or removal of excess iron due to blood transfusion. In the case of treating iron overload, they are usually administered by intravenous or intraperitoneal injection (Jomova, K., and Valko, M. 2011. *Importance of Iron Chelation in Free Radical-Induced Oxidative Stress and Human Disease. Curr Pharm Des* 17:3460-3473).

Currently, there is a novel class of iron chelators to prevent skin photoaging (Yiakouvaki, A., Savovic, J., Al-Qenaei, A., Dowden, J., and Pourzand, C. 2006. *Caged-iron chelators a novel approach towards protecting skin cells against UVA-induced necrotic cell death. J Invest Dermatol* 126:2287-2295). Under normal physiological conditions, this type of iron chelator has no ability to chelate iron. However, after exposure to UVA, it is activated and then chelates iron. This type of chelating agents is called "caged" iron chelator. Unfortunately, because they are chemicals, they may have different degrees of side effects on the skin.

Until now, the prior art has not specifically targeted iron in the skin. Therefore, from the clinical point of view, it is very important to search for better methods and products to remove iron in skin than chelating. The Chinese patent application CN1965801A disclosed skincare products, which were actually placed into two separate packages: Body Lotion and Revitalizing Factor. This patent application only considered the effective absorption of the ingredients and did not consider the effectual removal of iron. The body lotion is an emulsion with an acidic pH. The Revitalizing Factor is a powder with an alkaline pH. Because the acidic and alkaline properties of the two packages, they were not mixed together. In addition, this patent application used nanoparticles and nanoparticles might penetrate into the circulation system and cause toxicity.

SUMMARY OF THE INVENTION

Shortcomings of existing technologies in the current market of skincare products include: iron chelators' toxicity to the skin cells; lack of available skincare products that safely and effectively remove iron in the skin. Thus, current skincare products' anti-aging effects are limited. The present invention develops a novel class of skincare products that remove iron in the skin and provides a preparation method for them.

The technical solutions provided by the present invention are as follows:

The ingredients in the new skincare products include matrix and core components. The core components consist of a reducing agent(s) and a precipitating agent(s), wherein the molar ratio of the reducing agent to the precipitating agent is 1:3-6, preferably 1:5; core components in the skincare products represents 5%-10% w/w, preferably 5%; pH values of the skincare product is between 6.6 and 7.4, preferably 7; particle diameter of the skincare precipitating agent is in the submicron range (0.1-1 microns). In addition, the matrix is made of conventional skincare compounds;

Wherein the reducing agent is selected from vitamin C, vitamin E, glutathione, vitamin A, vitamin D, and their derivatives;

Wherein the precipitating agent is selected from calcium carbonate, pearl powder, magnesium carbonate, barium carbonate, calcium phosphate, magnesium phosphate, barium phosphate, calcium silicate, magnesium silicate, and barium silicate.

A method to prepare the novel class of iron-removing skincare products as stated in the present invention comprises the following steps:

1. Grind the particles of the precipitating agent to a particle size of 1-5 microns, preferably 1-3 microns;

2. Suspend the particles of the precipitating agent at a concentration of 100 mg/mL in deionized and nitrogen-saturated water and stir so that small particles float in the upper part and larger particles remain in the lower part of the container;

3. Slowly add the reducing agent into the bottom of the precipitating agent suspension. This is to use the acidity of the reducing agent to shrink the particle size of the precipitating agent into submicron particles. After the reaction is complete without bubbles simmering, gently heat the reaction mixture to 45° C. Under vacuum conditions, reduce the volume of the reaction mixture by about 50%. Obtain the skincare core components with a final molar ratio of the reducing agent to the precipitating agent between 1:3-6, preferably 1:5;

4. Put the core components into the matrix. After mixing, the core components represent 5%-10% (w/w). Adjust the pH to 6.6-7.4.

Wherein the stirring speed in step (2) is 200-500 rotation per minute;

Wherein the molar ratio of the reducing agent to the precipitating agent and the relative concentration of the core components in the skincare products play important roles in the ability of the skincare products to remove iron. If the amount of the precipitating agent exceeds that of the reducing agent, it could favor the reaction toward iron precipitation immediately after its reduction. The core components need to reach certain concentrations in order to effectively eliminate iron in the skincare products;

Wherein the particle size of the precipitating agent is critical; in the sub-micron range, the precipitating agent can penetrate into the epidermis of the skin, but not into the blood circulation system.

In this invention, the reducing agent is preferably vitamin C, while the precipitating agent is preferably calcium carbonate.

Figure 4:
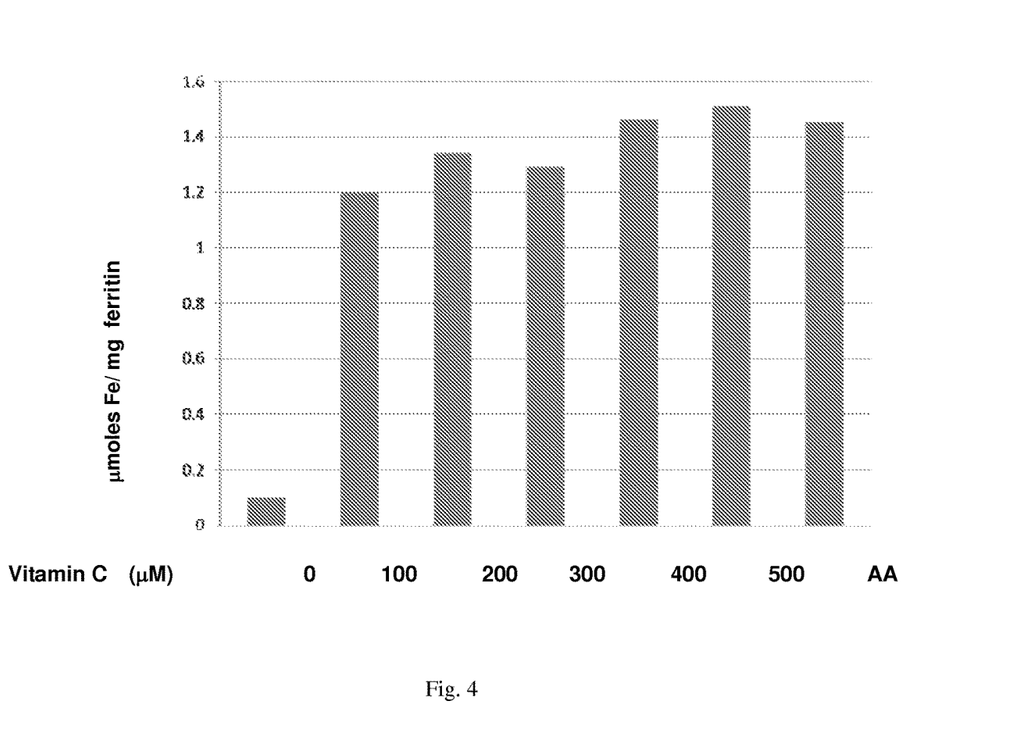
FIG. 4. Reducing effects of vitamin C on iron from ferritin.
Figure 5:
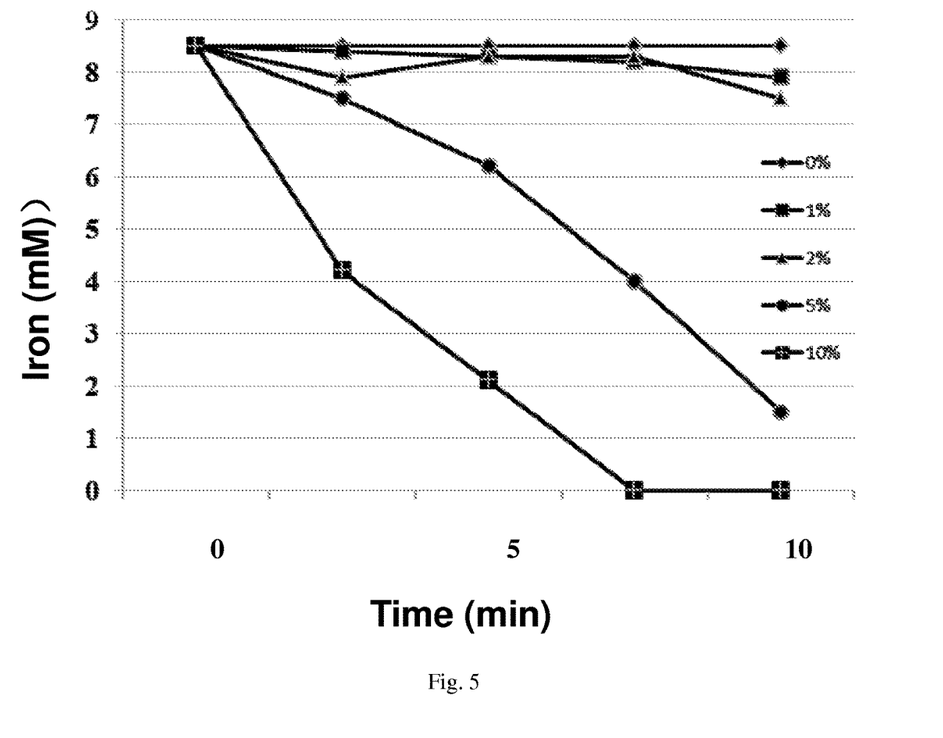
FIG. 5. Precipitating effects of calcium carbonate on iron.

Ferritin, one of the major proteins, sensitizes skin to sun exposure by strongly inducing matrix metalloproteinase (MMP-1) activity. Thus, the present invention is aimed to remove iron from ferritin. Ferritin has a strong binding affinity for trivalent (ferric) iron but no affinity for divalent (ferrous) iron. According to this physic-chemical characteristic, the present invention uses a reducing agent, such as vitamin C, to release iron from ferritin (FIG. 4). If only vitamin C is used, iron can be released from ferritin, but it can also continue to exert its harmful effect. To prevent this from occurring, the present invention employs a natural product calcium carbonate ($CaCO_3$) to precipitate the released iron (FIG. 5). Calcium carbonate is water insoluble and its neutral pH can easily cause iron precipitation immediately after its release from ferritin by vitamin C. Of course, if only calcium carbonate is used, it cannot effectively precipitate iron, because iron is still stored in ferritin.

Compared with the prior art, the beneficial effects of the present invention are as follows:

1. A mixture of vitamin C and calcium carbonate can effectively decrease iron-mediated ferritin formation (FIG. 6) as well as inhibit lipid peroxidation (FIG. 7) in primary normal human epidermal keratinocytes;

2. The present invention uses a mixture of vitamin C and calcium carbonate as a de-ironizing inducer (DII) and adds this mixture to the skincare products so that it makes up to 5%-10% (w/w) of the product. The high concentration of the core components is capable of reducing iron and precipitating iron and, thus, effectively removes iron from ferritin. Through the simultaneous use of the two natural products in two steps with the first step to reduce iron from ferritin, followed by precipitation of iron in the skin, this invention achieves the goal of preventing aging in postmenopausal skin.

Figure 8:
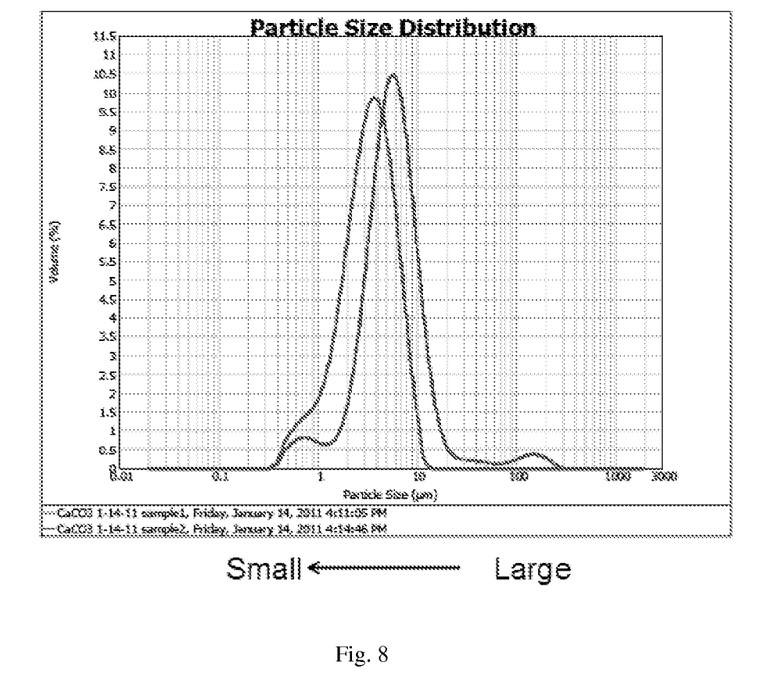
FIG. 8. Analyses of particle size of calcium carbonate with or without vitamin C treatment.
Figure 9:
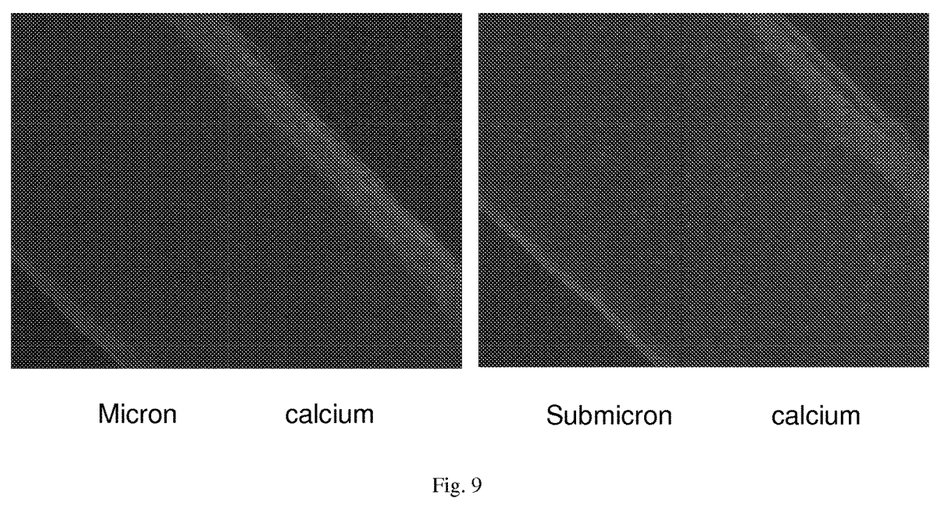
FIG. 9. Comparison of penetrations of submicron and micron particles of calcium carbonate into the three-dimensional skin model.
Figure 10:
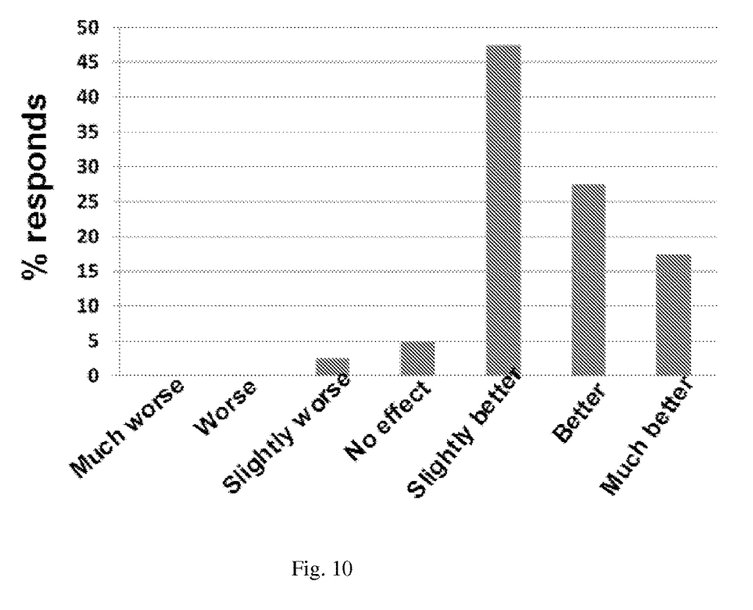
FIG. 10. Results from clinical trial questionnaire on satisfaction rate after using the skincare product of the present invention.
Figure 11:
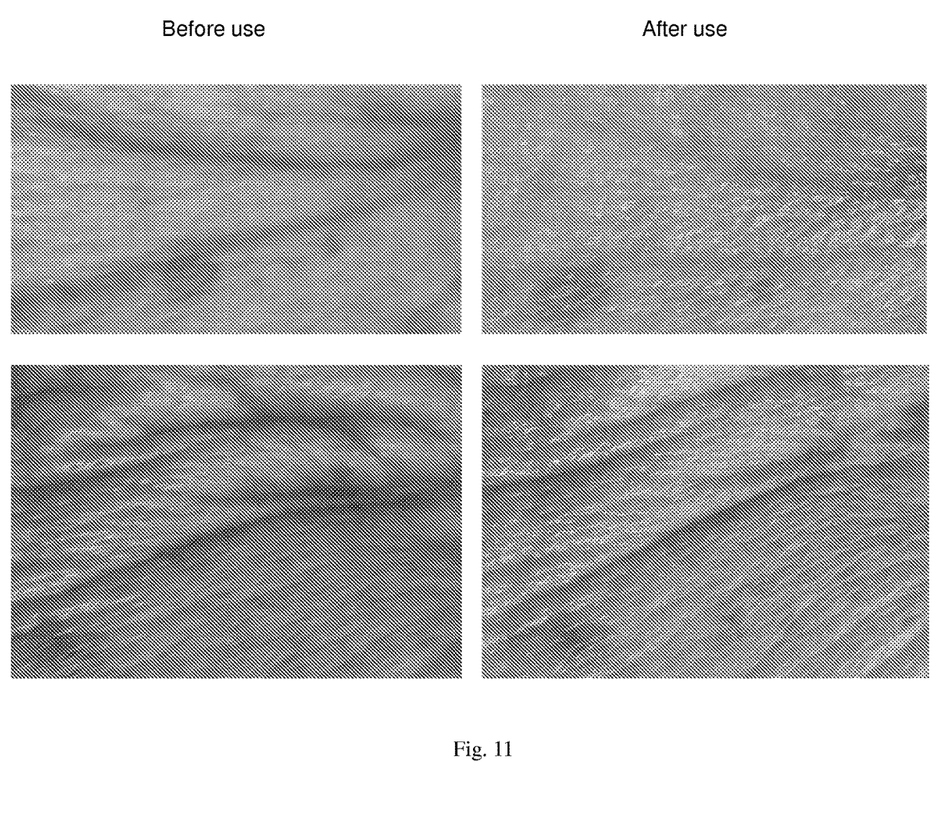
FIG. 11. Skin improvements after using the skincare product of the present invention.

3. The preparation method proposed in the present invention can powerfully produce submicron particles of calcium carbonate (FIG. 8), while preserving the reducing ability of the vitamin C. Vitamin C and calcium carbonate are premixed to produce sub-micron particles. These sub-micron particles can effectively enter into the skin (FIG. 9) and remove iron from the skin. Yet, they do not penetrate into the blood circulation system. The clinical trials showed that the mixture of the two can be the best in removing iron from the skin and preventing skin from aging (FIG. 10, FIG. 11).

4. The skincare products in the present invention have a neutral pH, which stabilizes vitamin C and calcium in the products.

DESCRIPTION OF EMBODIMENTS

In conjunction with the drawings and the embodiments, the present invention is further explained in details as below:

Embodiment 1

Changes in Estrogen and Ferritin Levels During Menopausal Transition:

Serum levels of 17β-estradiol (E2) were converted to % of peak value at 500 pg/mL serum at age 25. Levels of ferritin were expressed as ng/mL serum. E2 data as a function of age were obtained from web site www.drlam.com/A3R_brief_in_doc_format/Estrogen_Dominance.cfm Ferritin data were obtained from the Third National Health and Nutrition Examination Survey (NHANES III) in the United States (FIG. 1).

Human Studies:

Studies were performed after informed consent was obtained according to an approval from the local Institutional Review Board. Human skin 3 mm punch biopsy samples were obtained from six pre- and six post-menopausal women by punching the upper, inner left and right arms. Skin weights ranged from 3 to 50 mg. After grinding with a Dremel mini-Tissue Homogenizer in 400 μl M-PER lysis buffer in the presence of a protein inhibitor cocktail (Pierce Biotechnology Inc., Rockford, Ill.), protein extracts were collected after removing debris by centrifugation. The concentrations of total protein extracted from the skin samples were determined by bicinchoninic acid (BCA) assay. The remaining protein extracts were used for measurements of ferritin. Two data points (left and right arm) per subject were presented in the study. Results were expressed as ng ferritin per mg of total protein and are presented in FIG. 2. Mean age of post-menopausal women was 58.8±1.3 year old (n=5) and mean level of ferritin in the post-menopausal skin was 542.4 ng/mg protein. Mean age of pre-menopausal women was 41.6±1.7 year old (n=6) and mean level of ferritin in pre-menopausal skin was 381.6 ng/mg protein. It is noteworthy that one outlier from post-menopausal skin with a left arm ferritin of 2,360.2 ng/mg protein and a right arm ferritin of 989.0 ng/mg protein was excluded in the analyses. Otherwise, the difference would be even more significant (FIG. 2).

Figure 3:
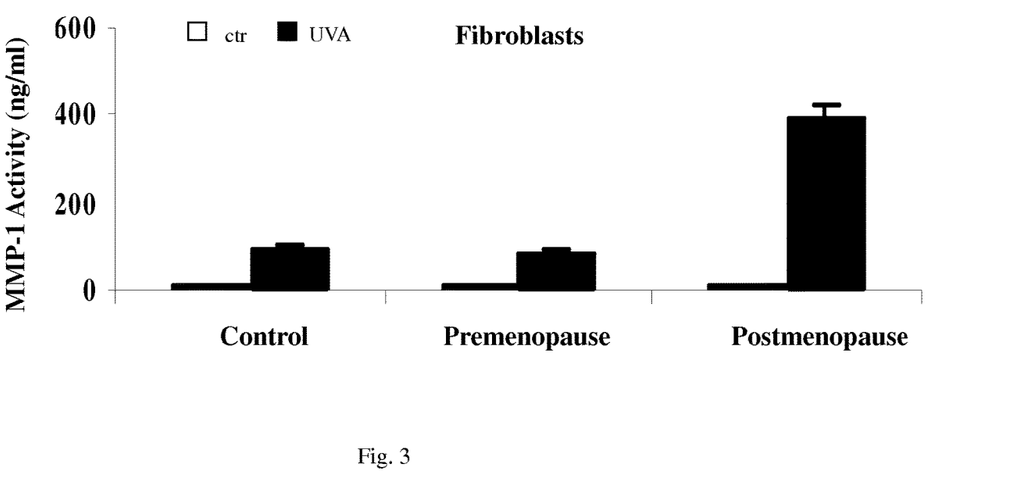
FIG. 3. Effects of UVA and iron on MMP-1 activities in primary human dermal fibroblasts.

Cell Culture and UVA Exposure:

Primary human dermal fibroblasts were seeded in 6-well plates and starved in 0.1% fetal bovine serum (FBS)-containing Dulbecco's Modified Eagle Medium (DMEM). According to FIG. 1, two cell culture conditions were developed with the low estrogen and high iron mimicking postmenopausal women and high estrogen and low iron simulating premenopausal women. In premenopausal condition (Pre-), level of 17β-estradiol (E2) in the cell culture media is 500 ng/ml and that of apo-transferrin (Tf, without iron) is 5 μg/ml. In postmenopausal condition (Post-), level of ferritin is 20 ng/ml and that of holo-Tf (iron is 100% saturated in the two binding sites of Tf) is 5 μg/ml. After overnight starving, fibroblasts grown under either the control, Pre-, or Post-conditions were exposed to UVA at 50 kJ/m². Media were collected 24 h later for measurements of matrix metalloproteinase-1 (MMP-1) activities. MMP-1 activities were measured by Förster resonance energy transfer (FRET) assay following the Manufacturer's protocol (AnaSpec, San Jose, Calif.). Briefly, 100 μl sample or 100 μl standard were added in the plate pre-coated with anti-MMP-1 antibody for 2 h. After washing, MMP fluorogenic substrate, 5-FAM/QXL™ 520 FRET peptide, were added and cultured for 16 h at room temperature. The fluorescence is measured at Ex/Em=490 nm/520 nm upon MMP-1-induced cleavage of the FRET substrate. Results show that there were no differences in background levels of MMP-1 in fibroblasts grown under Pre or Post-menopausal conditions. However, UVA significantly induced MMP-1 activities in primary human dermal fibroblasts grown under Post-condition as compared to fibroblasts grown under the control or Pre-conditions (FIG. 3).

Reduction of Iron from Ferritin by Vitamin C:

Ferritin at a concentration of 1 mg/ml was incubated with various concentrations of vitamin C (0-500 μM). After one hour incubation, the solutions were filtered using a membrane with a molecular weight cutoff of 5,000 Dalton (Millipore). Levels of iron in the filtrates were measured by Ferrozine (Sigma, St. Louis, Mo.), which forms a stable magenta-colored complex ($Fe^{2+}$-ferrozine) with a maximum absorption at 560 nm. In brief, 30 μl sample was added to 135 μl buffer. After 10 min incubation at 37° C., the absorbance was measured at 560 nm using a UV-visible microplate reader (SpectraMax Plus, Molecular Devices, Sunnyvale, Calif.). Then, 5 μl iron chromogenic agent (ferrozine) was added and after 15 min incubation, the absorbance was measured again at 560 nm. The difference in absorbance was used to calculate iron concentration after comparing to the iron standard curve. To determine whether iron is completely released from ferritin, atomic absorption (AA) was used to measure total iron in ferritin. Results show that high concentration of vitamin C is effective in releasing iron from ferritin. Atomic absorption (AA) confirmed that all iron in ferritin is released after vitamin C reduction (FIG. 4).

Precipitation of Iron by Calcium Carbonate:

Iron was added to extracellular matrix, followed by the addition of different concentrations of calcium carbonate (0-10%) (FIG. 5). After various time periods of incubation, a small part of the mixture was filtered using a membrane with a molecular weight cutoff of 5,000 Dalton as previously described in FIG. 4. Levels of iron in the filtrates were determined by Ferrozine. Results show that calcium carbonate can effectively precipitate iron in the cellular matrix.

Inhibition of Ferritin Formation by the Core Components:

Primary normal human epidermal keratinocytes (NHEK) were seeded in 6-well plates. The cells were pretreated with 50 μM ferrous sulfate for 4 h, followed by a mixture of vitamin C and calcium carbonate at 10 μg/cm² for 20 h. After washing, the cells were collected and the proteins were extracted in lysis buffer. After determining protein concentration, a small portion of the protein was used for the measurement of ferritin. Results show that a mixture of vitamin C and calcium carbonate can effectively decrease ferrous sulfate-induced ferritin formation in NHEK (FIG. 6).

Figure 6:
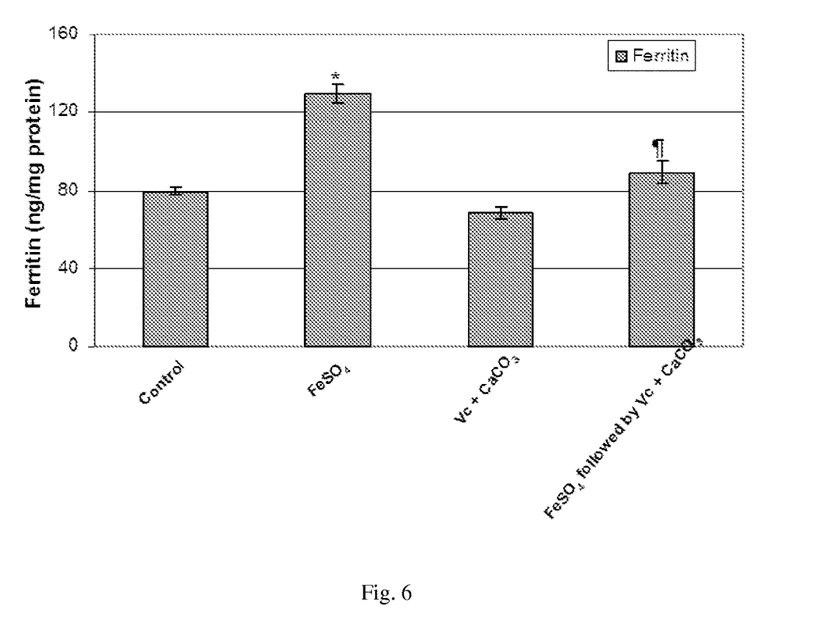
FIG. 6. Inhibition of ferritin formation by the core components of the invention.
Figure 7:
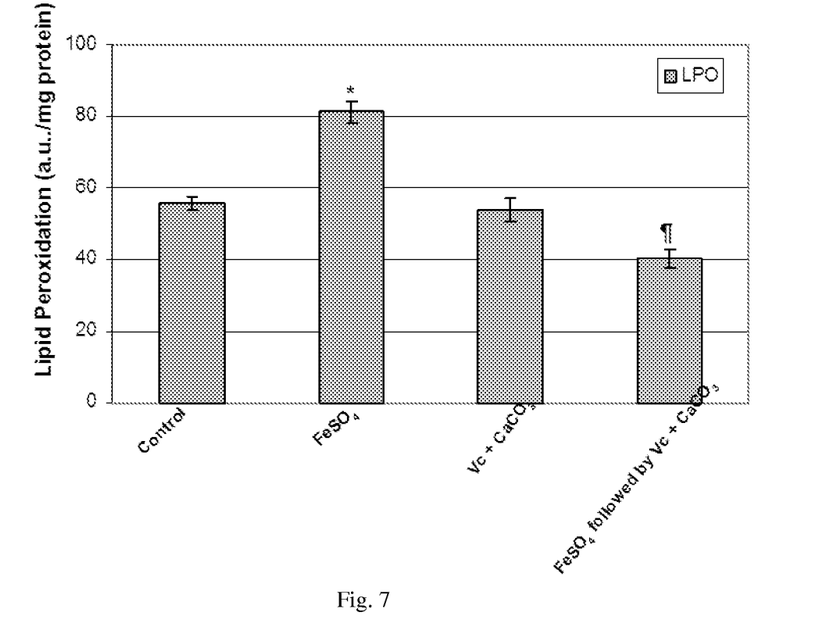
FIG. 7. Inhibition of lipid peroxidation by the core components of the invention.

Inhibition of Lipid Peroxidation by the Core Components:

NHEK cells were treated as described in FIG. 6. After centrifugation, cell debris was collected for measurements of lipid peroxidation using thiobarbituric acid assay. Results show that a mixture of vitamin C and calcium carbonate can effectively inhibit ferrous sulfate-induced lipid peroxidation in primary NHEK cells (FIG. 7).

Embodiment 2

Suspend calcium carbonate with particles size of approximate 2 μm at 100 mg per ml in deionized and nitrogen-saturated water.

1. Grind calcium carbonate to a particle size of approximately 2 μm; (2) Suspend calcium carbonate at 100 mg per ml in deionized and nitrogen-saturated water in order to avoid the oxidation of the mixture; stir slowly at 200-500 rounds per minute so that small particles float and the larger particles stay at the bottom; (3) At room temperature, add slowly 0.2 ml of 176 mg per ml of vitamin C to the bottom of the calcium carbonate suspension; use the acidity of vitamin C to reduce micron calcium carbonate particles to sub-micron particles; at the end of the reaction when there is no more bubbles, gently heat the reaction mixture to 45° C. and reduce the volume by about 50% under vacuum, and the molar ratio of the vitamin C to calcium carbonate is 1:5; (4) Add the core components, a mixture of vitamin C and calcium carbonate, into the matrix at 5% (w/w), and adjust PH to 7.

Embodiment 3

1. Grind calcium carbonate to a particle size of approximately 2 μm; (2) Suspend calcium carbonate at 100 mg per ml in deionized and nitrogen-saturated water in order to avoid the oxidation of the mixture; stir slowly at 200-500 rounds per minute so that small particles float and the larger particles stay at the bottom; (3) At room temperature, add slowly 0.33 ml of 176 mg per ml of vitamin C to the bottom of the calcium carbonate suspension; use the acidity of vitamin C to reduce micron calcium carbonate particles to sub-micron particles; at the end of the reaction when there is no bubbles, gently heat the reaction mixture to 45° C. and reduce the volume by about 50% under vacuum, and the molar ratio of the vitamin C to calcium carbonate is 1:3; (4) Add the core components, a mixture of vitamin C and calcium carbonate, into the matrix at 10% (w/w), and adjust PH to 7.

Embodiment 4

EFT 400 skin models were obtained from MatTek (Ashland, Mass.). Experiments were divided into two groups. One group is treated with 10 μg/cm$^2$ micron particles of calcium carbonate for 24 h; the other group is treated with 10 μg/cm$^2$ submicron particles of calcium carbonate for 24 h. After treatment, histological examination was carried out by hematoxylin and eosin staining and calcium levels penetrated into the skin were determined by alizarin staining, respectively. Results show that submicron calcium carbonate particles as prepared by the present invention are more readily that micron particles to enter the skin (FIG. 9).

Embodiment 5

Clinical trial participants used the skincare product of the present invention twice a day, once in the morning and once in the evening. After one month, participants were asked to conduct a survey of satisfaction after they used the product. Survey results show that satisfaction rate with reconstruction and stimulation of new collagen and formation of elastin is 93% (FIG. 10).

Embodiment 6

Clinical trial participants were required to take pictures at the corner of the right eye (canthus) before using the product of this invention, and then 3 months after continuous use of the product. Results show that canthus wrinkles after using the product of the invention is significantly reduced, highly improving skin appearance (FIG. 11).

The invention claimed is:

1. A skincare product configured to remove iron from the skin surface of a user, the skincare product comprising:
   a matrix and core components, the core components consisting of a reducing agent and a precipitating agent, wherein:
   the molar ratio of the reducing agent to the precipitating agent is 1:5;
   the core components in the skincare product represents 5%-10% w/w;
   the pH values of the skincare product is between 6.6 and 7.4; and
   wherein the reducing agent is selected from the group consisting of vitamin C, vitamin E, glutathione, vitamin A, vitamin D, and their derivatives; and
   wherein the precipitating agent is selected from the group consisting of calcium carbonate, pearl powder, magnesium carbonate, barium carbonate, calcium phosphate, magnesium phosphate, barium phosphate, calcium silicate, magnesium silicate, and barium silicate.

2. The skincare product according to claim 1, wherein the core components in the skincare products represents 5% w/w.

3. The skincare product according to claim 1, wherein the pH is 7.

4. The skincare product according to claim 1, wherein the precipitating agent is in particle form.

5. The skincare product according to claim 4, wherein the precipitating agent particles are in the submicron range and can penetrate into the epidermis of the skin but not into the blood circulation system.

6. A skincare product configured to remove iron from the skin surface of a user, the skincare product comprising a matrix and core components, the core components consisting of vitamin C and calcium carbonate present in a molar ratio of 1:5; the core components being 5%-10% w/w of the skincare product; and the pH of the skincare product being 7.

* * * * *